United States Patent [19]
Roth

[11] Patent Number: 5,415,646
[45] Date of Patent: May 16, 1995

[54] ONE USE SAFETY LOCKING SYRINGE

[76] Inventor: Noah M. Roth, 24 Sutton Pl., Islandia, N.Y. 11722

[21] Appl. No.: 240,580

[22] Filed: May 11, 1994

[51] Int. Cl.6 .......................... A61M 5/50; A61M 5/32; A61M 5/31
[52] U.S. Cl. ................................. 604/110; 604/195; 604/240
[58] Field of Search ............... 604/110, 192, 195, 196, 604/240

[56] References Cited

U.S. PATENT DOCUMENTS

| | | | |
|---|---|---|---|
| 4,969,877 | 11/1990 | Kornberg | 604/195 |
| 5,026,354 | 6/1991 | Kocses | 604/195 |
| 5,163,907 | 11/1992 | Szuszkiewicz | 604/110 |
| 5,256,151 | 10/1993 | Chul | 604/195 |
| 5,267,962 | 12/1993 | Jenson | 604/110 |
| 5,279,580 | 1/1994 | Wallingford | 604/195 |
| 5,308,329 | 5/1994 | Mazur et al. | 604/110 |
| 5,328,484 | 7/1994 | Somers et al. | 604/195 |
| 5,342,323 | 8/1994 | Haining | 604/195 |

*Primary Examiner*—John D. Yasko
*Assistant Examiner*—Adam J. Cermak

[57] ABSTRACT

A syringe to be used within the health care profession providing protection against inadvertent needle sticks and accidental reuse of contaminated syringes. The syringe contains two sets of locking mechanisms. One is located on the needle assembly, permanently locking it to the plunger when said plunger is fully depressed. Another set is located at the top of the cylindrical barrel, permanently locking the plunger which is now attached to the needle assembly, within the barrel.

5 Claims, 2 Drawing Sheets

ONE USE SAFETY LOCKING SYRINGE

FIELD OF INVENTION

This invention relates to hypodermic syringes in which the needles are retracted into either the plunger and, or barrel. When used properly this invention will prevent accidental reuse and needle sticks common in trauma centers and general practice alike.

BACKGROUND OF THE INVENTION

Many attempts have been made to design a practical hypodermic syringe with a retractable needle. Examples of such are shown in U.S. Pat. Nos. 4,838,863; 4,950,241; 4,978,343; 5,019,044; 5,064,419; 5,180,370; 5,273,543.

These patents show various designs but they all lack a straight forwardness, simplicity, reliability, in both use and fabrication, along with a self containment of all its parts. The need for such a syringe comes about from the recent rise of and concern in the transfer of infectious diseases such as AIDS, and Hepatitis. In trauma centers and emergency rooms, as well as any other area where syringes are used procedure concerning the proper disposal of syringes may not be followed. This may be due to the urgency of the situation or negligence. Lawsuits against health care facilities by workers or patients is also a factor in today's society. The legal liability aspect gives an economic incentive for a reliable, and affordable syringe of the aforementioned type.

OBJECTS OF THE INVENTION

The primary object of this invention is to provide a hypodermic syringe with a retractable needle which is simple, reliable and will securely retain the needle within the barrel of the syringe thus preventing accidental needle sticks.

Another object of this invention is to have a syringe with a retractable needle wherein the needle assembly is attached to the plunger when the plunger is in its fully depressed position. This plunger needle assembly is then locked within by another set of locking mechanisms rendering the syringe unusable.

Still a further object of this invention is to provide a hypodermic syringe which is inexpensive to manufacture and simple to use.

SUMMARY OF THE INVENTION

This invention is a safety hypodermic syringe comprising of a hollow barrel having a rear opening and a front end opening. A hollow needle protruding through the front end of the barrel to permit fluid in the barrel to be injected through the needle. A slidable plunger is positioned in a fluid tight engagement within the inside surface of the barrel. Engagement structure is provided for allowing the end of the plunger to engage and lock to the needle assembly allowing axial directed forces to withdraw the needle assembly within the barrel of the syringe. Moving the now plunger-needle assembly rearwardly out of the front end opening of the barrel into a stored position within the barrel, and a means to retain the plunger-needle assembly within the stored position of the barrel is provided preventing the needle from protruding from the front end of the barrel. Transition between the first locking position and the second locked stored position withdrawing the needle assembly into the barrel is accomplished by one motion of the plunger with respect to the barrel. After the plunger is locked to the needle assembly it is then withdrawn in an axial direction within the barrel to the second stored locked position.

DETAILED DESCRIPTION

Figure 1:
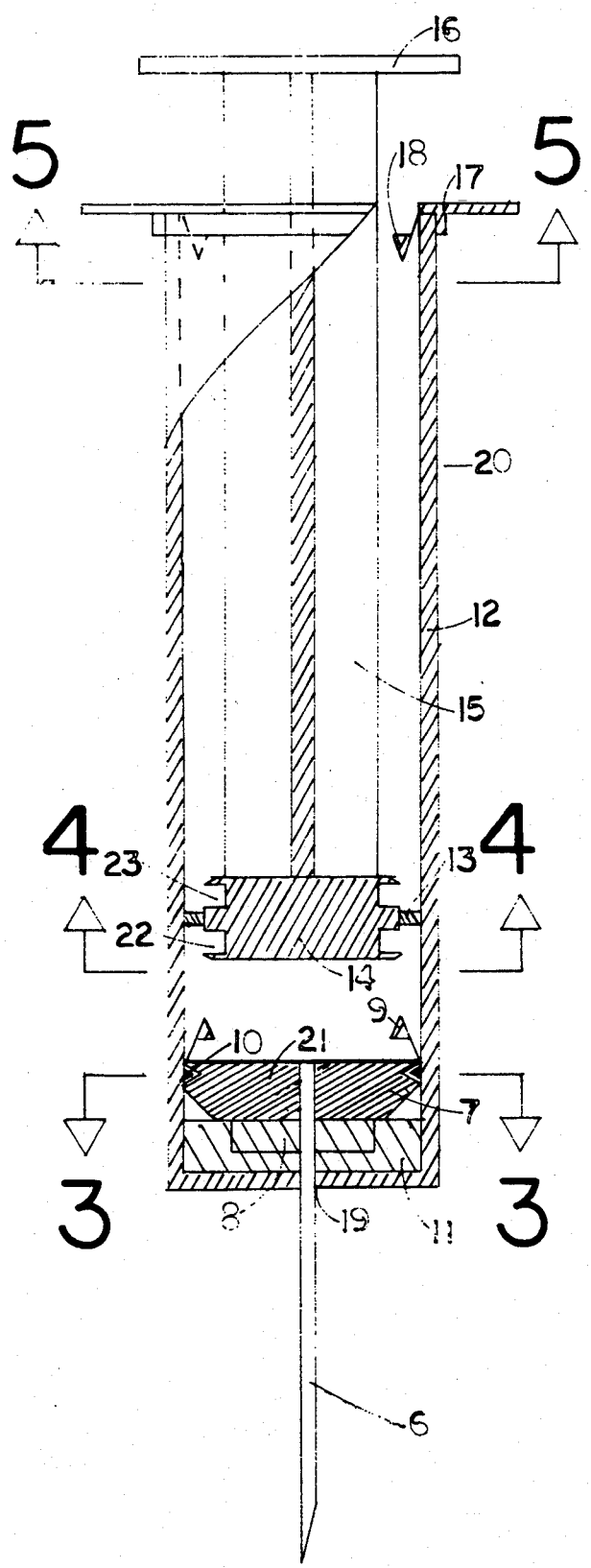
FIG. 1 is a cross sectional side elevation view of a syringe illustrating an embodiment of the invention with portions broken away to show the internal mechanisms of the invention.

While the invention is satisfied in many different forms, there are shown in the drawings and will herein by described preferred embodiments of the invention with the understanding that it to be considered exemplary of the principles of the invention and is not intended to limit the scope of the invention to the embodiments illustrated. The scope of the invention will be measured by its appended claims and their equivalent.

For the purposes of the description of this invention the term "distal end" is to refer to the end of the syringe of which the needle projects. Whereas the term "proximal end" is intended to refer to the end of the syringe closest to the holder of the syringe and furthest away from the tip.

Referring to the drawing in particular FIG. 1 which show a manually retractable locking needle embodiment of a hypodermic syringe indicated generally by numeral 20. The syringe 20 has a hollow cylindrical barrel 12 which is open at the proximal end, and is lined with elastomeric seal ring 11 with center hole 19 to allow the needle to project out of barrel 12.

Figure 2:
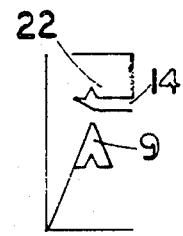
FIG. 2 is an enlarged partial view of FIG. 1 illustrating the locking member and key member within the syringe (typical of four), special note being made to matching recessed and raised groove.
Figure 3:
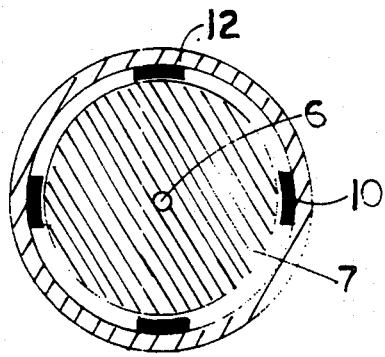
FIG. 3 is a cross sectional view taken on line 3—3 of FIG. 1 showing the internal mounting means of the barrel provided to secure needle assembly within syringe, while in use.

Secured within barrel 12, by mounting means 10 shown cross sectionally in FIG. 3 is needle assembly 7 which includes head member 21 containing circumferencial grooves, with corresponding structure to that of mounting means 10, as shown in FIG. 1, to facilitate the securing of needle assembly 7 within the barrel 12, and needle 6 molded therein extended radially outward through center hole 19 sealed with elastomeric ring 8 in barrel 12. Head member 21 contains two locking mechanisms 9 who's enlarged view is shown in FIG. 2 these locks fasten into groves 22 within plunger.

Figure 5:
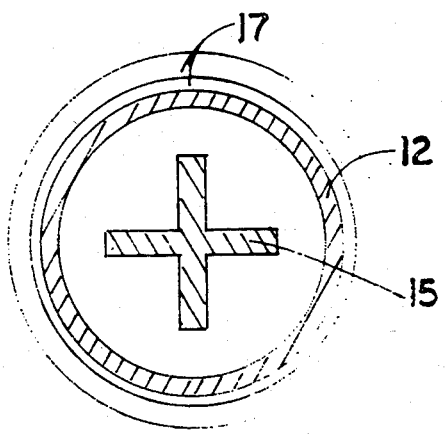
FIG. 5 is a cross sectional view taken on line 5—5 of FIG. 1.

The barrel 12 has an radially outwardly extending flange 17 which is fastened to barrel by adhesive or comparable means shown in cross section FIG. 5. Flange 17 also contains two upper locking members 18 similar to mechanisms 9 described above, fastening into key members 23 of plunger. Flange 17 aids in holding barrel 12 while depressing plunger 15, by depressing on enlarged plate 16 of plunger.

Figure 4:
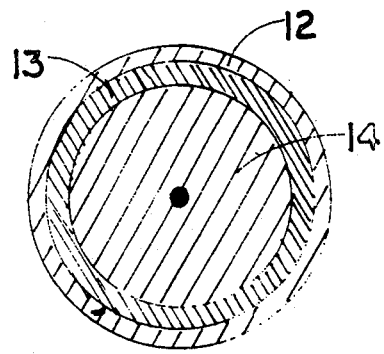
FIG. 4 is a cross sectional view taken on line 4—4 of FIG. 1.

The plunger 15 fits inside barrel 12 and is movable axially backward and forward within the barrel. Annular seal ring 13, as shown in FIG. 4 surrounds plunger head 14 providing a seal with the inner wall surface of barrel 12 to retain injection fluid and pressure. Disc shaped plunger rod flange 16 is provided as a convenience for moving the plunger with respect to the barrel 12.

Plunger head 14 contains four key members (2) 22, (2) 23 for engagement purposes with lock members 9, and 18 in a snap fit arrangement as shown in FIG. 2. After injection is completed and axial forces are applied in the proximal direction of the syringe, the syringe needle assembly 7 becomes disengaged from barrel 12 via. locking mechanisms 9. In the plunger-needle assemblies final position it will engage with locking mechanism 18 securing the syringe within barrel 12.

An important feature of this invention is the self containment of all its working pans, and the simplicity of its use requiring only the normal axial forces applied when giving injections.

It must be noted that the forces required in giving an injection (i.e. piercing of the skin with needle). Is less than the forces required to disengage needle assembly 7 from engagement snaps 10.

The present invention can be used in the same manner as a conventional hypodermic syringe following known and accepted safe use procedures. In giving an injection the syringe 20 is first filled with fluid medication by inserting the needle into a container of fluid and pulling the plunger rearwardly in barrel 12. The needle 6 is inserted into the patient and the plunger is depressed a sufficient distance into barrel 12 to expel the fluid medication from the barrel thereby engaging locking members 9 on needle assembly 7 into key members 22. The needle 6 is then withdrawn from the patient and the plunger is pulled axially in the proximal direction until locking members 18 have engaged with key members 23 of plunger head 14.

Thus it can be seen that the present invention provides a simple, straight forward, reliable, easily fabricated syringe allowing the needle to be withdrawn and locked inside the barrel using axial forces such as those used for drawing liquid into the syringe. The invention also provides similar locking mechanisms for holding the needle assembly within the syringe.

The barrel, plunger and other main components of the invention shown herein are made preferably of plastics which can be made by injection molding or other suitable means of manufacturing. It should also be recognized that the detailed contours and proportions of the various components can vary from some of the illustrations shown in the drawings without departing from the scope of the invention. These and various other modifications can be made in the embodiments shown and described herein without departing from the scope of the invention.

I claim:

1. A safety hypodermic syringe comprising:
   A) a hollow syringe barrel for containing injection fluid, said barrel comprising a proximal end including a proximal end opening, a distal end including a distal end opening, and an interior barrel surface;
   B) a piston for sealingly engaging said interior barrel surface, said piston comprising a first key member and a second key member;
   C) means for mounting a needle to the syringe barrel, said mounting means for temporarily securing said needle within the distal end of said syringe barrel with said needle extending forwardly from the distal end of said syringe barrel, said mounting means further comprising a first lock member for engaging said first key member, such that when said first key member and said first lock member are engaged proximal movement of said piston in and relative to said barrel moves said mounting means proximally;
   D) said syringe further comprising a second lock member for engaging said second key member, such that when said piston is moved proximally in and relative to said barrel said second key member engages said second lock member and prevents subsequent distal movement of said piston in and relative to said barrel;
   E) said first lock member and said second lock member having substantially the same locking structure.

2. The safety hypodermic syringe as set forth in claim 1, wherein said mounting means further comprises means for temporarily locking said mounting means adjacent said distal end opening.

3. The safety hypodermic syringe as set forth in claim 1, wherein said first key member and said first lock member interlock, and said second key member and said second lock member interlock.

4. The safety hypodermic syringe as set forth in claim 1, said mounting means further comprising means for snapingly securing said mounting means to said syringe barrel, wherein the force required to unsnap said securing means from said syringe barrel is greater than the force required to penetrate skin with said needle.

5. The safety hypodermic syringe as set forth in claim 1, wherein said piston has an range of motion within said barrel adequate to fill said barrel with injection fluid, eject air trapped within said barrel, and administer a required dosage.

* * * * *